(12) United States Patent
Stella et al.

(10) Patent No.: US 9,827,203 B2
(45) Date of Patent: *Nov. 28, 2017

(54) COATED SOLID DOSAGE FORMS

(71) Applicant: The Procter & Gamble Company, Cincinnati, OH (US)

(72) Inventors: Mark Edward Stella, Cincinnati, OH (US); Elissa Nicole Knights, Pleasant Ridge, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/218,099

(22) Filed: Jul. 25, 2016

(65) Prior Publication Data

US 2016/0331690 A1  Nov. 17, 2016

Related U.S. Application Data

(63) Continuation of application No. 13/371,652, filed on Feb. 13, 2012, now Pat. No. 9,421,171.

(60) Provisional application No. 61/442,435, filed on Feb. 14, 2011.

(51) Int. Cl.
| | |
|---|---|
| *A61K 9/28* | (2006.01) |
| *A61K 47/46* | (2006.01) |
| *A61K 31/135* | (2006.01) |
| *A61K 31/167* | (2006.01) |
| *A61K 31/485* | (2006.01) |
| *A61K 31/09* | (2006.01) |
| *A61K 9/20* | (2006.01) |
| *A61K 31/137* | (2006.01) |
| *A61K 31/192* | (2006.01) |

(52) U.S. Cl.
CPC ............ *A61K 9/288* (2013.01); *A61K 9/2068* (2013.01); *A61K 9/282* (2013.01); *A61K 9/2886* (2013.01); *A61K 9/2893* (2013.01); *A61K 31/09* (2013.01); *A61K 31/135* (2013.01); *A61K 31/137* (2013.01); *A61K 31/167* (2013.01); *A61K 31/192* (2013.01); *A61K 31/485* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 3,780,185 A | 12/1973 | Fields | |
| 5,356,650 A | 10/1994 | Kanayama | |
| 6,277,409 B1 * | 8/2001 | Luber | A61K 9/2893 424/476 |
| 2007/0231387 A1 * | 10/2007 | Levi | A61K 9/0056 424/472 |
| 2008/0131467 A1 | 6/2008 | Nelson et al. | |
| 2009/0196925 A1 * | 8/2009 | Brady | A61K 9/286 424/479 |
| 2009/0197974 A1 | 8/2009 | Ahmed et al. | |
| 2010/0266687 A1 | 10/2010 | Willoughby | |
| 2011/0070287 A1 | 3/2011 | Nielsen et al. | |

FOREIGN PATENT DOCUMENTS

| | | | | |
|---|---|---|---|---|
| WO | WO 2009/055846 A1 | 5/2009 | | |
| WO | WO 2009055846 A1 * | 5/2009 | ............ | A61K 9/2027 |

OTHER PUBLICATIONS

David W. Ball. The Chemical Composition of Honey. Journal of Chemical Education vol. 84 No. Oct. 10, 2007, 1643-1646.*
Wang et al., "A Review of Process Simulations and the use of Additives in Spray Drying", Food Research International, vol. 42, No. 1, pp. 13-25, Jan. 2009.
PCT International Search Report dated Apr. 18, 2012.
All Office Actions for U.S. Appl. No. 13/371,652, filed Feb. 13, 2012.

* cited by examiner

*Primary Examiner* — Frederick Krass
*Assistant Examiner* — Michael P Cohen
(74) *Attorney, Agent, or Firm* — Amanda Herman; Alexandra S. Anoff

(57) ABSTRACT

The invention is associated with ingestible film coated solid dosage forms comprising natural honey in the coating applied to such forms. The natural honey of the film coated solid dosage form is of sufficient level to be perceived by the user while avoiding sticking to each other or the packaging with which they are in contact and, or storage.

19 Claims, 1 Drawing Sheet

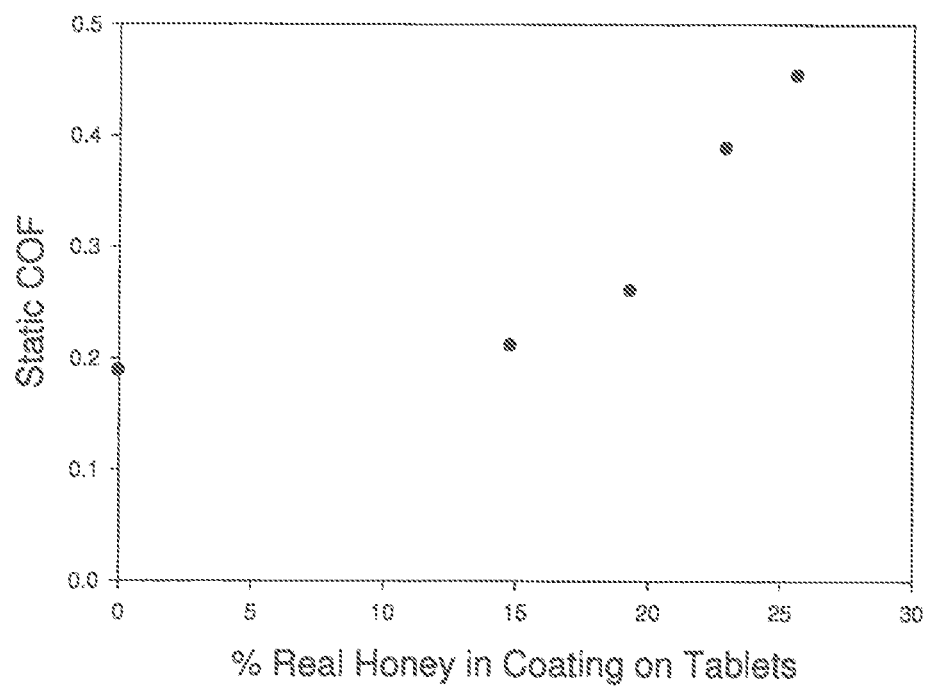

COATED SOLID DOSAGE FORMS

FIELD OF THE INVENTION

The invention is associated with ingestible film coated solid dosage forms comprising natural honey in the coating applied to such forms. The natural honey of said ingestible film coated solid dosage form is of sufficient level to be perceived by the user while avoiding sticking to each other or the packaging with which they are in contact and, or storage.

BACKGROUND OF THE INVENTION

Oral medicaments can assume a variety of dosage forms. Non-limiting examples of the most common solid dose forms include tablets, caplets, softgel capsules, solid-filled capsules, liquid-filled capsules, enteric-coated forms, sustained-release forms, solid lozenges, liquid-filled lozenges, mouth and throat drops, effervescent tablets, orally disintegrating tablets and combinations thereof. Oral compositions are typically swallowed immediately, or slowly dissolved in the mouth. These dosage forms may contain efficacious ingredients that have a disagreeable taste. Even for example upon compressing medicaments into a hardened tablet, the medicaments may provide the tablet with a disagreeable taste and, or odor. To overcome such bad flavors, solid dosage forms may be coated with materials including sugar or other sweeteners.

In the case of compressed tablets, the tablet cores are placed into coating pans where coating liquids are poured or sprayed over the tablet cores as they rotate in the pans. A repeated number of applications of the coating are made to achieve a determined coating thickness and pleasing aesthetic appearance. The coating's thickness is determined by a number of factors including masking any present objectionable taste, making the tablets easier to swallow and contributing to a specified dissolution rate of the tablets to effectuate dissolution in a target portion of the gastrointestinal tract for the optimum efficacy of the medicaments in the tablets.

Useful film coatings are generally thin and comprise crosslinked polymers. These coatings may comprise sweeteners and flavors, such as natural honey. Natural honey is an appealing flavor since consumers favor its taste and also perceive it as a safe and effective ingredient that positively impacts health and wellness.

Notwithstanding the implied positives, using natural honey in film coatings at levels sufficiently high that the tablets are realistically considered by consumers to contain natural honey, offers its own set of challenges when used in a film coating. Not the least of these challenges is that there is an inherent tackiness or stickiness of natural honey. Consumers have experienced this when dispensing liquid natural honey when used in one's home.

Even when a film coating containing natural honey dries, it is believed that the surface of the solid dosage form would remain noticeably sticky. This would not only creates a negative experience when consumers handle film coatings containing honey but it also would presents challenges when the solid doses are being packaged by the manufacturer. For example, typical tablet filling equipment comprises a bulk hopper where the solid dosage form such as tablets are fed from the hopper to packaging equipment for transferring the tablets into packaging such as bottles. Tablets must rapidly move to a filling portion of the packaging machine wherein the tablets are accumulated in a specified number and transferred into each bottle. Traditionally repeating rows of individual pockets for the solid dosage form are filled and eventually collected to be placed into the bottles. It is important, therefore, that the tablets freely flow from the hopper into the tablet collecting section of the machine and from there are dropped into the package. Even if sticky solid dosage forms were to be packaged on blistering equipment, possibly by hand, the tablets must slide freely over a sheet of polyethylene blister card into pockets of the card to fill each pocket before adhering to the blister card's foil or paper back sheet. If the solid dosage form adheres to the package or in the case of their being in bulk, to each other, there is a definite consumer negative since the solid dosage form is difficult to dispense and possibly may corrupts the designed solubility of solid dosage form in terms of its desired dissolution in the gastrointestinal tract making the tablet's ingredients less bioavailability than designed.

Therefore, there remains an unmet need to include significant levels of natural honey in film coatings on solid dosage forms that avoids anticipated problems associated with its inherent stickiness.

SUMMARY OF THE INVENTION

A solid dosage form comprising: a film coating wherein the film coating comprises greater than 0% to about 25% natural honey; and an inner core; wherein the solid dosage form has a static coefficient of friction value of less than about 0.40.

A tablet comprising: a film coating wherein the film coating comprises greater than 0% to about 25% flavor wherein the flavor is natural honey and from about 0.05% to about 5% sweetener; and an inner core comprising an active; wherein the solid dosage form has a static coefficient of friction value of less than about 0.40 and wherein the tablet tastes like honey.

DESCRIPTION OF FIGURE

The FIGURE is a graph illustrating the relationship between the level of natural honey in the film coating of the solid dosage form such as a tablet and the static coefficient of friction associated with that tablet when tested using the method disclosed herein.

DETAILED DESCRIPTION OF THE INVENTION

The present invention relates to solid dosage forms with a film coating that contains natural honey. The film coating provides the consumer with a strong perception of honey flavor, while the film dosage forms are not so sticky as to deter efficient packaging and eventual handling by the consumer.

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference. Unless otherwise noted, the percentage of the materials used in the solid dosage forms of this invention are by total weight of the respective elements of the film coating or the inner core of the solid dosage form.

As previously mentioned, solid dosage forms may include a variety of product forms. Non-limiting examples of the most common solid dose forms include, but are not limited to compressed tablets, caplets, softgel capsules, solid-filled capsules, liquid-filled capsules, enteric-coated forms, sustained-release forms, solid lozenges, liquid-filled lozenges, mouth and throat drops, effervescent tablets, orally disintegrating tablets and combinations thereof. In one example the solid dosage form is a compressed tablet. In another example, the solid dosage form is not a softgel capsule or a liquid-filled capsule.

Solid dosage forms are typically swallowed immediately, or slowly dissolved in the mouth. Regardless of their form, the solid dosage form is essentially coated in a similar manner to that described below for coating compressed tablets.

Tablets to be coated are typically manufactured for sale using high speed equipment or machines to efficiently compress large numbers of tablets into solid dosage forms referred to as tablet cores. Tableting machines generally referred to as a tablet presses are well known in the art. Granulation is fed into the press' hopper by either by scooping or gravity feed through tubes from a granulation transport located in a mezzanine above the press. As the granulation enters the press' hopper an auger distributes it evenly in a consistent flow of granulation onto the press' table. A typical rotary press comprises a round metallic table having a series of consecutive holes about the periphery of the table. Tableting dies that dictate the shape of the resulting compressed tablets are locked into the table's holes by set screws. The dies, open at both ends, accommodate a set of complementary shaped lower punches to prevent the granulation fed into the die from falling or spilling out the bottom of the die. The table rotates as granulation is fed filling the dies. As the table continues to rotate, a second set of complimentary upper punches individually enters each die and are forced downward by a cam roller, compressing the granulation into a designed size and shape. While still rotating, the upper punches pull out of the die as the lower punches rise to push the compressed tablet core out of the die wherein it is directed to a discharge chute and collected in an appropriate receptacle. The compression forces acting on the punches is established by the press operator to provide a desired hardness. Tablet press operators constantly check the tablet cores' thickness, weight, hardness and visual condition, making adjustments as necessary to produce tablets within designed specifications at low incidents of defects. This process is repeated until the supply of granulation is exhausted.

Coating the inner core of a solid dosage form involves pouring bulk product such as a tablet cores into spherical coating pans having an access port on one side of the pan. Upon placing bulk product into the pans, the pans rotate wherein the equipment operator applies series of measured aliquots of film coating either by hand or automatically through nozzles suspended on booms within the pans. The film coating is applied to the tumbling product on a specific schedule for even coating, allowing the product to dry between applications. As a result the coating is a series of very thin coatings that form an aesthetically pleasing a smooth, even film coated product surface free of defects such as mottling or orange peeling.

Film coatings of the solid dosage forms of the present invention can comprise a honey flavor. Honey flavor can be selected from the group comprising natural honey, artificial honey, synthetic honey, freeze dried honey, powdered honey solids, and combinations thereof. In one example, the honey flavor is natural honey. Natural honey can hide any disagreeable flavors associated with the product medicaments and consumers believe it has inherent health benefits especially compared to other sweeteners such as refined sugar or artificial sweeteners such as Aspartame®. Natural honey is increasingly being used in medicinal preparations, as well as food and beverage compositions. As used herein, the term "natural honey" includes products made by bees (*Apis mellifera* L.) or other insects from the nectar of plants or from secretions of living parts of plants that the bees collect, transforming it by combining substances of their own that they deposit, dehydrate, store and leave in the honey comb to ripen and mature including naturally occurring cellulosic enzyme.

A supplier of natural honey, Symrise Inc., lists that one of their honey products comprises from 45% to 55% natural honey as well as 45% to 55% propylene glycol, 1% to 3% water, 0.5% to 1% natural flavor, and less than 0.5% disodium EDTA as a preservative. In one example, the honey flavor is not an artificial honey, synthetic honey, freeze dried honey, or powdered honey solids. In another example, the flavor consists of natural honey flavor. In one example, the natural honey is a liquid before it is combined with other ingredients and processing steps to form the film coated tablets. In one example, the film coating contains natural honey and artificial honey, synthetic honey, or another honey flavor that is not natural honey.

As previously mentioned, the taste of natural honey is an important signal to the consumer to reinforce its advertised use in a solid dosage form. Therefore, the more natural honey in the film coating the stronger the signal and the more positively the product is received by the consumer. When the level is too high, however, it is believed that the coated solid dose will eventually reach a point where the solid dosage form becomes sticky. As discussed above, when natural honey in film coatings result in being sticky and tacky, manufacturers and consumers alike will be discouraged from making and using respectively such film coated solid dosage forms. Given the consumer's interest to use natural honey containing film coated dosage forms, however, the applicants have striven to develop a film coating that while providing the consumer with a strong perception of honey, the film coated solid dosage forms are not so sticky as to deter efficient packaging and eventual handling by the consumer. The film coated dosage forms have levels of honey so as not to be objectionably sticky as determined by measuring the tablets' static coefficient of friction value or hereinafter referred to as the "static COF" of the solid dosage form.

The static COF is a dimensionless scalar value that describes the ratio of the force of friction between two bodies and the force pressing them together. The static COF is measured by the following method:

Test Method for Determining Film Coated Tablet Static Coefficient of Friction

The test is conducted at room temperature of about 20° C. to about 25° C. and atmospheric relative humidity from about 40% to about 50%. The instrument for measuring the frictional forces of the film coated tablets is the 32-07 Series Friction Tester, manufactured by Testing Machines Inc. The instrument comprises a weighted sled that is in directly attached to the machine's pulling arm by a pin. The arm pulls the sled across an aluminum platen attached to the chassis of the Tester. The weighted sled's mass is 1360 grams or 3 pounds. The method of determining the static COF value of film coated solid dosage form such as a coated compressed tablet is determined using the following method:

1. clean the platen's aluminum surface by wiping the surface with alcohol swab and allow the platen to dry;
2. place a film coated tablet on about the center of the platen;
3. place the sled over the tablet on the platen, taking precautions to allow the sled to only rest on the top surface of the tablet;
4. insert the sled's connecting pin into the pulling arm's bushing and lock the anti-skid arm in the down position therein maintaining the pulling arm's lateral motion as it crosses the platen in a straight line;
5. start the sled's movement wherein the Tester records the static COF value which is the value at the point immediately before the film coated tablet starts to be dragged laterally across the platen; and
6. repeat the test on two more film coated tablets from the same coating pan, add all the values and divide by three to obtain the static COF value of the film coated tablets.

The relationship of the level of natural honey used in the film coating and the static COF is plotted on the graph corresponding to the FIGURE. The graph in the FIGURE plots the static COF of the film coated tablets of the present invention on the y-axis and the percent of natural honey in the film coating by weight of the film coating on the x-axis. This graph illustrates the nearly linear relationship of these two factors wherein upon reaching a certain percentage of natural honey in the film coating, its corresponding static COF determines whether the performance of the film coated tablets is acceptable in terms of being successfully packaged and handled by consumer without being sticky.

The calculation for determining the percentage of honey, as shown on the x axis of the FIGURE, is as follows: The Symrise Natural Honey flavor 229946 is a mixture of real honey and propylene glycol at about a 50:50 percentage. Therefore, the calculation of percentage honey takes into account the amounts of color coating, sweetener and propylene glycol in the coating ingredients, to determine the percentage of real honey in the coating on the tablet.

According to the graph in the FIGURE, the maximum level of natural honey in the tablet's film coating is about 25% corresponding to the maximum static COF of the product for successful packaging and handling or a static COF value of about 0.40. It is assumed that the minimum level of natural honey consumers will recognize and taste in a film coating is about 10% by total weight of the film coating prior to its application. The discrete data points on the graph correspond to Examples 1 through 5 described hereafter.

The range of natural honey in the film coating of the tablets of the present invention is greater than 0% to about 25%, alternatively from about 10% to about 25%, alternatively about 13% to about 23%, alternatively about 13% to about 20%, and alternatively from about 13% to about 18% by total weight of the film coating at a static COF value less than 0.40, alternatively less than 0.35, alternatively less than 0.30, alternatively less than 0.25, alternatively less than 0.20. In another embodiment the static COF can be at a level of about 0.15 to about 0.40. In another embodiment the static COF can be at a level of about 0.15 to about 0.35. In an additional embodiment, the static COF can be at a level of about 0.15 to about 0.30.

Additional Film Coating Ingredients

Film coating has a number of ingredients that are important in making successfully coated solid dosage forms that have a pleasing appearance as well as functionally provide the designed bioavailability of medicaments that are intended to deliver to the consumer. In one example, the film coating does not contain gelatin. The film coating of the present invention can comprise polymeric materials and a compatible delivery vehicle for the dissolution and distribution of the polymeric materials. Additionally most film coatings also comprise adjunct sweeteners, colorants and flavorants in addition to the natural honey.

The selection of the polymeric material(s) does not favor those that hinder the perception of flavor by the consumer due to "trapping" the flavors including that of the natural honey in the coating. The polymeric materials are usually dissolved in a vehicle to be delivered wherein upon delivery to a surface, the polymers experience cross linking of the polymeric chains to make up the polymer. These linkages are frequently covalent bonds, hydrogen bonds that cross-link and lay flat making a smooth film coating. This coating aids in the swallowing and taste masking of the tablet. The polymeric materials for use in the present include polymers selected from the group consisting of hypromellose, hydroxyethyl cellulose, hydroxymethyl cellulose, carboxymethylcellulose sodium, hydroxypropyl cellulose, polyethylene glycol, ethylcellulose and mixtures thereof. Also useful in the film coating of the present invention are enteric polymers selected from the group consisting of hypromellose phthalate, polyvinyl acetate phthalate, cellulose acetate phthalate, polmethacrylates, shellac and mixtures thereof. The film coating comprises polymeric materials from about 5% to about 30%, alternatively from about 10% to about 22%, alternatively from about 15% to about 20% by total weight of the film coating prior to its application.

Lastly polymeric materials usually incorporate plasticizers to enhance the flexibility and or pliability of the cross-linked polymer. This is important when coating solid dosage forms so the coating completely envelops the variety shapes and sizes solid dosage forms presently found in commerce. Plasticizers are selected from the group consisting of polyols such as glycerol, propylene glycol, polyethylene glycol (PEG); organic esters including phthalate esters; dibutyl sebacete and citrate esters; castor oil; acetylated or/and monoglycerides; fractioned coconut oils and mixtures thereof.

A liquid vehicle delivers the polymeric material and all of the other ingredients comprising the solid dosage forms film coating. Environmental impact and economic considerations enter the decision of the selected vehicle; however, the foremost decision resides in which vehicle is most compatible and useful with the polymeric materials. The vehicle is selected from the group consisting of water, alcohols, ketones, esters and mixtures thereof, but generally water is used. The film coating comprises a vehicle that is from about 50% to about 95%, alternatively from about 70% to about 90%, alternatively from about 80% to about 85% by total weight of the film coating prior to its application.

Notwithstanding the presence of natural honey in sufficiently high levels in the present invention sweeteners may optionally be added to the film coating of the present invention. In another example, sweeteners can be added to the inner core of the solid dosage forms. In one example, the coating, the inner core, and/or the solid dosage form is substantially free of artificial sweeteners. In one example, honey is not present in the inner core. Suitable sweeteners for use herein can include aspartame, saccharin and its salts, Sucralose™ (sold by the McNeil Specialty Products Co., New Brunswick, N.J.); Prosweet™ (sold by the Virginia Dare Extract Co., New York, N.Y.); Magnasweet™ (sold by MAFCO Worldwide Corp., Licorice Division, Camden, N.J.); ammonium glycyrrhizinate and its salts, Talin™ (thaumatin) and its diluted products, such as Talin GA90, (sold by the Talin Food Company, Birkenhead, England); and Acesulfame K, or mixtures thereof. In one example, the sweetener is Sucralose. In one example, the film coating can comprise sweeteners from about 0.05% to about 5%, alternatively from about 0.10% to about 2%, alternatively from about 0.25% to about 1.0% by total weight of the film coating prior to its application.

Other flavoring agents that may be used in the film coating and/or the core of the present invention. Other flavoring agents can include anise, oil of peppermint, oil of clove, eucalyptus, lemon, lime, honey lemon, red fruit, mint, grapefruit, orange, cherry cola or mixtures thereof. The film coating and/or the core may comprise flavoring agents from about 0.05% to about 25%, alternatively from about 0.1% to about 20.0%, alternatively from about 2.5% to about 15.0%, and alternatively from about 2.5% to about 8% by total weight of the film coating prior to its application or by total weight of the core.

Colorants can also be added to the film coating and/or the core. Colorants are selected by one skilled in the art for a number of reasons including marketing of the product. It has herein been found that certain colors assist in providing a signal to consumers regarding the content of the solid dosage form. The colorants may be natural or synthetic dyes and pigments selected from the group consisting of organic dyes and their lakes, iron oxide pigments, titanium dioxide, talc, anthrocyanins, carmine, riboflavin, and mixtures thereof. In one example, the solid dosage form does not comprise synthetic dyes or synthetic pigments. In one example, the film coating can comprise a yellow or a honey coloring. The film coating may comprise colorants from about 0.05% to about 3.0%, alternatively from about 0.5% to about 2.0%, alternatively from about 0.5% to about 1.5% to about 0.5% by total weight of the film coating prior to its application.

In one example, the solid dosage form contains no gluten.

Actives

The solid dosage form can comprise actives. The actives can be contained in the film coating and/or the inner core. In one example, the film coating is substantially free of actives. Non-limiting examples of actives can include actives suitable for use with a respiratory condition, actives suitable for use with gastrointestinal conditions, vitamins, minerals, elements, plant-derived materials, energy-boosting materials, probiotics, supplements, fiber, prebiotics, and combinations thereof. Such actives are grouped generally below for ease of presentation, but as would be understood by those of skill in the art, there is overlap in usage of many of the actives described herein—for example such actives as anti-inflammatory and/or pain actives which can be used with respiratory conditions, gastrointestinal conditions, muscle and joint conditions, menstrual conditions and the like. When used in the inner core, prescription or non-prescription actives can be administered according to a prescribed regimen and can be combined in a system or kit with additional, non-prescription actives as disclosed in co-pending patent application U.S. Ser. No. 12/971,677, filed Dec. 17, 2010.

The solid dosage forms can comprise from greater than 0% to about 90%, alternatively from about 0.0001% to about 75%, alternatively from about 0.001% to about 50%, alternatively from about 0.01% to about 25%, alternatively from about 0.01% to about 15%, and alternatively from about 0.01% to 10% active, by weight of the solid dosage form. In another example, the inner core can comprise from about 0.5% to about 70%, alternatively from about 1% to about 65%, alternatively from about 10% to about 60%, and alternatively from about 25% to about 55% pharmaceutical active, by weight of the inner core.

The solid dosage forms can comprise from about 0.001 mg to about 1000 mg, alternatively from about 2.5 mg to about 750 mg, alternatively from about 5 mg to about 650 mg, alternatively from about 10 mg to about 550 mg, alternatively from about 25 mg to about 500 mg, alternatively from about 50 mg to about 400 mg, alternatively from about 100 mg to about 375 mg, and alternatively from about 200 mg to about 350 mg of the active, per solid dosage form.

The solid dosage forms can be administered in a single daily dose or multiple daily doses. In one example, the solid dosage forms are administered every twelve hours, in another example one time every eight hours, in another example one time every six hours, in another example one time every four hours, and in another example the user can administer the solid dosage forms whenever they are needed.

The solid dosage form can comprise one or more actives suitable for use with a respiratory condition. Respiratory conditions encompass a broad range of conditions, including viral infections such as cold and flu, bacterial infections, as well as allergies, sinusitis, rhinitis, asthma, and the like. Respiratory conditions may present with any of a variety of symptoms, such as runny nose, nasal and/or chest congestion, cough, sneezing, pressure, headache, aches, fever, fatigue and/or sore throat. Actives suitable for use with a respiratory condition can treat or mitigate these symptoms and generally fall into the following classifications: decongestants, anti-cholinergics, expectorants, antihistamines, antitussives, pain relievers, anti-virals, mucolytics, demulcents, anesthetics, and antibiotics. Such actives can include non-prescription pharmaceutical actives and prescription pharmaceutical actives. Such solid dosage forms can be prepared by any known or otherwise effective technique as would be understood by those of skill in the art such as those described in this application as well as U.S. 2009/0082316.

Non-limiting examples of decongestants can include pseudoephedrine, pseudoephedrine hydrochloride, phenylephrine, phenylephrine hydrochloride, phenylpropanolamine, oxymetazoline, xylometazoline, naphazoline, l-desoxyephedrine, ephedrine, propylhexedrine, and combinations thereof; non-limiting examples anticholinergics can include ipratropium, chlorpheniramine, brompheniramine, diphenhydramine, doxylamine, clemastine, triprolidine, and combinations thereof; non-limiting examples of expectorants can include guaifenesin, ambroxol, bromhexine, and combinations thereof; non-limiting examples of antihistamines can include chlorpheniramine, desloratadine, levocetirizine, diphenhydramine, doxylamine succinate, triprolidine, clemastine, pheniramine, brompheniramine, dexbrompheniramine, loratadine, cetirizine, fexofenadine, amlexanox, alkylamine derivatives, cromolyn, acrivastine, ibudilast, bamipine, ketotifen, nedocromil, omalizumab, dimethindene, oxatomide, pemirolast, pyrrobutamine, pentigetide, thenaldine, picumast, tolpropamine, ramatroban, repirinast, suplatast tosylate aminoalkylethers, tazanolast, bromodiphenhydramine, tranilast, carbinoxamine, traxanox, chlorphenoxamine, diphenylpyaline, embramine, p-methyl-diphenhydramine, moxastine, orphenadrine, phenyltoloxamine, setastine, ethylenediamine derivatives, chloropyramine, chlorothen, methapyrilene, pyrilamine, talastine, thenyldiamine, thonzylamine hydrochloride, tripelennamine, piperazines, chlorcyclizine, clocinizine, homochlorcyclizine, hydroxyzine, tricyclics, phenothiazines, mequitazine, promethazine, thiazinamium methylsulfate, azatadine, cyproheptadine, deptropine, isothipendyl, olopatadine, rupatadine, antazoline, astemizole, azelastine, bepotastine, clemizole, ebastine, emedastine, epinastine, levocabastine, mebhydroline, mizolastine, phenindamine, terfenadine, tritoqualine, and combinations thereof; non-limiting examples of antitussives (i.e. cough suppressants) can include dextromethorphan, menthol, codeine, chlophedianol, levodropropizine, and combinations thereof; non-limiting examples of pain relievers, can include acetaminophen, ibuprofen, ketoprofen, diclofenac, naproxen, aspirin, and combinations thereof, as well as prescription analgesics, non-limiting examples of which include propyxhene HCl, codeine, mepridine, and combinations thereof; non-limiting examples of anti-virals can include amantidine, rimantadine, pleconaril, zanamivir, oseltamivir, and combinations thereof; non-limiting examples of mucolytics can include ambroxol, N-acetylcysteine, bromhexine, and combinations thereof; non-limiting examples of demulcents can include glycerin, honey, pectin, gelatin, slippery elm bark, liquid sugar, glycyrrhizin (licorice), and combinations thereof; non-limiting examples of anesthetics can include phenol, menthol, dyclonine HCl, benzocaine, lidocaine, hexylresorcinol, and combinations thereof; non-limiting examples of antibiotics can include nitroimidazole antibiotics, tetracyclines, penicillin-based antibiotics such as amoxicillin, cephalosporins, carbopenems, aminoglycosides, macrolide antibiotics, lincosamide antibiotics, 4-quinolones, fluoroquinolones, rifamycins, macrolides, nitrofurantoin, and combinations thereof; and any pharmaceutically acceptable salts, metabolites, and combinations thereof of the above-listed actives.

In one example, the solid dosage form comprises one or more of the following: decongestants, expectorants, antihistamines, antitussives, and pain relievers. In one example the solid dosage form comprises a decongestant, an expectorant, an antitussive, and a pain reliever. In another example the solid dosage form comprises a decongestant, a pain reliever, and an antitussive. In one example, the decongestant is selected from the group consisting of pseudoephedrine hydrochloride, phenylephrine hydrochloride, and combinations thereof. In one example, the expectorant can be guaifenesin. In one example, the antihistamine can be chlorpheniramine. In one example the antitussive can be selected from the group consisting of dextromethorphan, codeine, and combinations thereof. In one example the pain relievers can include acetaminophen, ibuprofen, or combinations thereof. In one example, the dosage unit can be formulated as a daytime formula and can further comprise caffeine which is a stimulant. In another example, the dosage unit can be formulated as a nighttime formula and comprise a sedative and/or be formulated without a stimulant In one example, the dosage units comprise one or more actives suitable for use with a respiratory condition, in another example the dosage units comprise two or more actives suitable for use with a respiratory condition, in another example the dosage units comprise three or more actives suitable for use with a respiratory condition, and in another example the dosage units comprise four or more actives suitable for use with a respiratory condition. In one example, the dosage unit comprises exactly one active suitable for use with a respiratory condition, in another example exactly two actives suitable for use with a respiratory condition, in another example exactly three actives suitable for use with a respiratory condition, and in another example exactly four actives suitable for use with a respiratory condition. In one example the dosage units comprise acetaminophen, dextromethorphan, and phenylephrine. In another example the dosage units comprise acetaminophen, dextromethorphan, phenylephrine, and guaifenesin.

The solid dosage form can comprise one or more actives suitable for use with a gastrointestinal condition. Actives suitable for use with a gastrointestinal condition can treat or mitigate gastrointestinal symptoms and generally fall into the following classifications: anti-diarrheal actives, laxatives, antacids, anti-flattulent/anti-gas agents, H2 receptor antagonists, proton pump inhibitors, and anti-inflammatories.

Non-limiting examples of actives suitable for use with gastrointestinal conditions can include: Non-limiting examples of anti-diarrheal actives can include loperamide, bismuth-containing compositions, bismuth subsalicylate, colloidal bismuth subcitrate, bismuth subcitrate, kaolin, pectin, clays such as attapulgite, activated charcoal, and combinations thereof; non-limiting examples of laxatives can include fiber, resistant starch, resistant maltodextrin, pectin, cellulose, modified cellulose, polycarophil, senna, sennosides, bisacodyl, sodium phosphate, docusate, magnesium citrate, mineral oil, glycerin, aloe, castor oil, magnesium hydroxide, and combinations thereof; anti-nausea and antiemetic agent, non-limiting examples of which include bismuth containing compositions, phosphated carbohydrates, diphenhydramine, cyclizine, meclizine, and combinations thereof; non-limiting examples of antacids can include sodium bicarbonate, sodium carbonate, calcium carbonate, magnesium carbonate, magnesium hydroxide, aluminum hydroxide, magnesium silicates, alginic acids, sodium alginate, magaldrate, and combinations thereof; non-limiting examples of anti-flattulent/anti-gas agents can include simethicone, activated charcoal, lactase, alpha-galactosidase enzymes, and combinations thereof; non-limiting examples of H2 receptor antagonists can include famotidine, ranitidine, ciemtidine, nitazidine, and combinations thereof; non-limiting examples of proton pump inhibitors can include omeprazole, lansoprazole, esomeprazole, pantoprazole, rabeprazole, and combinations thereof; non-limiting examples of anti-inflammatories can include mesalamine; and any pharmaceutically acceptable salts, metabolites, and combinations thereof; rafting agents non-limiting examples of which include alginates; pectins and polysaccharides, and combinations thereof of the above-listed actives.

The solid dosage forms can comprise one or more vitamins, including but not limited to provitamin and all forms of Vitamins C, D, A, B, E, and combinations thereof. In one example, the vitamin is Vitamin C in the form of ascorbic acid or the equivalent of a salt of ascorbic acid or the equivalent of a derivative of ascorbic acid. In one example, the Vitamin C can be an immediate release form and in another example the Vitamin C can be in a sustained release form.

Nonlimiting examples of Vitamin D can include Vitamin D3 (cholecalciferol), Vitamin D2 (ergocalciferol) and combinations thereof. Additional, nonlimiting examples also include metabolites of Vitamin D, including calcidiol, calcitriol, and combinations thereof. The Vitamin D, including cholecalciferol, ergocalciferol, calcidiol and calcitriol, may be derived from synthetic or natural sources. Vitamin D, including cholecalciferol and calcitriol, may be sourced from an extract of solanum glaucophyllum (malacoxylon), trisetum flavescens (goldhafer) or cestrum diurnum. Both the pure Vitamin D and/or glycosides of the Vitamin D, may be used.

Non-limiting examples of the Vitamin A useful in the present invention can include vitamin A, retinol, retinyl palmitate, retinyl acetate, retinyl proprionate, beta-carotene, alpha-carotene, beta-cryptoxanthin, and mixtures thereof.

Non-limiting examples of Vitamin B can include Vitamin B1 (thiamin), Vitamin B2 (Riboflavin), Vitamin B3 (niacin), Vitamin B5 (pantothenic acid), Vitamin B6 (pyridoxine, pyridoxal, or pyridoxamine), Vitamin B7 (Biotin), Vitamin B9 (Folic acid), Vitamin B 12 (cyanocobalmin), and combinations thereof. In one example, the inner core of the solid dosage forms can comprise Vitamin E. Vitamin E is a lipid soluble antioxidant and provides defenses against cellular oxidative damage. The term "Vitamin E" typically includes eight different chemical forms: four tocopherols and four tocotrienols. The most active form of Vitamin E is alpha-tocopherol.

When certain vitamins, (also certain minerals, metals, elements and the like), are included as components in the solid dosage forms, the actual amounts of many of these components, in grams per unit dose, are often extremely small, and make the individual components difficult to handle, measure and process. Therefore such components are commonly prepared or purchased as a premix in or on a carrier such as sucrose or lactose. With respect to the weight percent of a given vitamin as a percent of a premix or vitamin-carrier mix, such percentages can vary greatly depending on the vitamin and the amount of vitamin desired, as would be understood by one of skill in the art. Generally, however, for vitamins in or on a carrier, the vitamin can comprise, as a weight percent of vitamin to carrier, from about 0.0001% to about 50%, alternatively from about 0.001% to about 45%, alternatively from about 0.001% to about 40%, by weight of the vitamin-carrier composition.

The solid dosage forms can comprise minerals, metals and/or elements. Non-limiting examples of minerals, metals, and elements useful in the systems of the present invention include: zinc, iron, calcium, iodine, copper and selenium. When present, the minerals, metals and/or elements can be on or in a suitable carrier, and comprise from about 1% to about 50% by weight and alternatively from about 2% to about 30%, by weight of the composition comprising the mineral, metal or element and the carrier. The minerals, metals, and elements can be administered in a single daily dose or multiple daily doses.

The solid dosage forms can comprise plant-derived materials. As used herein, non-limiting examples of plant-derived materials include those used in traditional native American, Chinese, Aryuvedic and Japanese medicine, including flowers, leaves, stems and roots of plants as well as extracts and isolated active components from the flower, leaves, stems, and roots of plants. Some particularly useful plant-derived materials include, but are not limited to, Andrographis (Andrographis paniculata), Garlic (Allium sativum L.), Eleutherococcus senticosus (Siberian ginseng), Ginseng (American ginseng, Asian ginseng, Chinese ginseng, Korean red ginseng, Panax ginseng: Panax ssp. Including P. ginseng C.C. Meyer, and P. quinquefolius L.), Propolis, Slippery elm (Ulmus rubra Muhl, Ulmus fulva Michx), quercetin (a flavanol), and combinations and/or mixtures thereof. Particularly useful plant-derived materials are those that have beneficial respiratory, gastrointestinal, overall health and energy effects. The plant-derived materials can be administered in a single dose or multiple daily doses.

Other plant-derived materials can exert beneficial effects on the gastrointestinal tract, non-limiting examples of which include soothing or demulcent effects, gas reducing or carminative effects, anti-diarrheal or astringent effects, laxative or aperient, cathartic, purgative or hydrogogue effects, analgesic, antispasmodic or relaxation effects, stimulant or bitter effects, or digestive aiding effects. Non-limiting examples of such other plant-derived materials useful in the methods and systems include the ginger Family (Zigiberaceae), licorice root (Glycyrrhizin glabra), marshmallow root (Althea officinalis, Althea radix), Chamomile (Matricariae flos, Chamaemelum nobile), Fennel oil, Fennel Seed (Foeniculum vulgare), Caraway oil, Caraway seed (Carum carvi, Carvi fructus, Carvi aetheroleum), Lemon Balm (Melissae folium, Melissa), Horehound Herb (Murrubii herba), Flaxseed alpha-linoleic acid (Lini semen), and combinations thereof.

The solid dosage forms can comprise materials having energy boosting/enhancing benefits. Such energy benefits are useful for overall health and well-being, as well as being useful in treating conditions such as respiratory and gastrointestinal conditions, to provide individuals afflicted with such conditions with more energy or a perception of more energy to enable such individuals to maintain their daily routines while treating a condition such as a respiratory or gastrointestinal condition. Non-limiting examples of such materials include the following, many of which have multiple benefits including benefits for respiratory and gastrointestinal conditions: caffeine (a stimulant and diuretic), Vitamin B complex, green and black tea (which can be used for stimulant and diuretic properties of the caffeine contained therein), taurine, rhodiola rosea, Siberian ginseng (Eleutherococcus senticosus), Vitamin C, iron, CoQ10, L-carnitine, L-Theanine, Vitamin D, guarana (Paullinia cupana), magnesium, Schizandra chinensis, Yerba Mata (Ilex paraguariensis), Goji (Wolfberry), quercetin (a flavanol), amalaki (Indian gooseberry), acai (from genus Euterpe), maca (Lepidium meyenii), ginkgo biloba, glucuronolactone, panax ginseng (from species within Panax, a genus of 11 species of slow-growing perennial plants with fleshy roots, in the family Araliaceae), Echinacea (genus of nine species of herbaceous plants in the Family Asteraceae), rooibos (Aspalathus linearis), DHEA, aromas and aromatherapy, noni (Morinda mangosteen (Garcinia mangostana), and selenium. The energy boosting material can be administered in a single daily dose or multiple daily doses. The inner core of the solid dosage forms can comprise from about 1 µg to about 10 g, alternatively from about 1 mg to about 5 g, and alternatively from about 100 mg to about 5 g of energy-boosting/enhancing material, per inner core of the solid dosage form.

The solid dosage forms can comprise a probiotic. In one example, the inner core comprises probiotics. Proboitcs can be useful in treating and/or preventing respiratory conditions, treating and/or preventing gastrointestinal conditions, as well as providing overall health benefits. As used herein, "probiotic" includes natural and/or genetically modified microorganisms, viable or dead; processed compositions of micro-organisms; their constituents and components such as proteins and carbohydrates or purified fractions of bacterial ferments; that beneficially affect a host. The general use of probiotics herein is in the form of viable cells. However, use can be extended to non-viable cells such as killed cultures or compositions containing beneficial factors expressed by the probiotic. Killed cultures may include thermally killed microorganisms, or microorganisms killed by exposure to altered pH or subjected to pressure. For the purpose of the present invention, "probiotic" is further intended to include metabolites generated by the microorganisms during fermentation, if they are not separately indicated. These metabolites may be released to the medium of fermentation, or they may be stored within the microorganism. As used herein "probiotic" also includes bacteria, bacterial homogenates, bacterial proteins, bacterial extracts, bacterial ferment supernatants, and mixtures thereof, which perform beneficial functions to a host animal when given at a therapeutically effective amount.

Non-limiting examples of probiotic bacteria suitable for use herein can include strains of *Streptococcus lactis, Streptococcus cremoris, Streptococcus diacetylactis, Streptococcus thermophilus, Lactobacillus bulgaricus, Lactobacillus acidophilus, Lactobacillus helveticus, Lactobacillus bifidus, Lactobacillus casei, Lactobacillus lactis, Lactobacillus plantarum, Lactobacillus rhamnosus, Lactobacillus delbruekii, Lactobacillus thermophilus, Lactobacillus fermentii, Lactobacillus salivarius, Lactobacillus reuteri, Lactobacillus brevis, Lactobacillus paracasei, Lactobacillus gasseri, Pediococcus cerevisiae, Bifidobacterium longum, Bifidobacterium infantis, Bifidobacterium adolescentis, Bifidobacterium bifidum, Bifidobacterium animalis, Bifidobacterium pseudolongum, Bifidobacterium thermophilum, Bifidobacterium lactis, Bifidobacterium bulgaricus, Bifidobacterium breve, Bifidobacterium subtilis, Escherichia coli* and strains of the genera including *Bacillus, Bacteroides, Enterococcus* (e.g., *Enterococcus faecium*) and *Leuconostoc*, and mixtures and/or combinations thereof. As a portion of the compositions of the inner core of the solid dosage forms, the probiotic, as a freeze-dried powder (as would be understood by one of skill in the art) can comprise from about 1% to about 50%, alternatively from about 1% to about 40%, alternatively from about 1% to about 30%, and alternatively from about 2% to about 20%, by weight of the composition of the inner core of the solid dosage forms. The probiotic can be administered in a single daily dose or multiple daily doses.

The solid dosage forms can also comprise fiber. Fiber can be useful in treating and/or preventing gastrointestinal conditions, as well as providing overall gastrointestinal health benefits. As used herein, the term "fiber" means carbohydrate polymers including those naturally occurring in food as consumed; those having been obtained from food raw material by physical, enzymatic or chemical means; and synthetic carbohydrate polymers, which are resistant to digestion and absorption in the small intestine and have partial fermentation in the large intestine. Non-limiting examples of fibers and analogous carbohydrate polymers can include pectins, psyllium, guar gum, xanthan gum, alginaes, gum arabic, fructo-oligosaccharides, inulin, agar, beta-glucans, chitins, dextrins, lignin, celluloses, non-starch polysaccharides, carrageenan, reduced starch, and mixtures and/or combinations thereof. In one embodiment, the fiber is glucose polymers, preferably those which have branched chains. Among such suitable fibers is one marketed under the tradename "Fibersol2", commercially available from Matsutani Chemical Industry Co., Itami City, Hyogo, Japan. Other non-limiting examples of suitable fibers include oligosaccharides, such as inulin and its hydrolysis products commonly known as fructo-oligosaccharides, galacto-oligosaccharides, xylo-oligosaccharides, and oligo derivatives of starch. The fiber can be administered in a single daily dose or multiple daily doses. The inner core of the solid dosage forms can comprise from about 10 mg to about 100 g, alternatively from about 50 mg to about 50 g, alternatively from about 100 mg to about 50 g, alternatively from about 500 mg to about 50 g, and alternatively from about 1 g to about 40 g of fiber, per inner core of the solid dosage form.

The solid dosage forms can comprise a prebiotic. Prebiotics can be useful in treating and/or preventing gastrointestinal conditions, as well as providing overall gastrointestinal health benefits. As used herein, the term "prebiotic" includes substances or compounds that beneficially affect the host mammal by selectively promoting the growth and/or activity of one or more probiotic bacteria in the gastro-intestinal tract of the host animal, thus maintaining normal health or improving health of the host. Typically, prebiotics are carbohydrates, (such as oligosaccharides), but the term "prebiotic" as used herein does not preclude non-carbohydrates. Many forms of "fiber" exhibit some level of prebiotic effect. Thus, there is considerable overlap between substances that can be classified as "prebiotics" and those that can be classified as "fibers".

Non-limiting examples of prebiotics suitable for use in the compositions and methods can include psyllium, fructo-oligosaccharides, inulin, oligofructose, galacto-oligosaccharides, isomalto-oligosaccharides, xylo-oligosaccharides, soy-oligosaccharides, gluco-oligosaccharides, mannan-oligosaccharides, arabinogalactan, arabinxylan, lactosucrose, gluconannan, lactulose, polydextrose, oligodextran, gentioligosaccharide, pectic oligosaccharide, xanthan gum, gum arabic, hemicellulose, resistant starch and its derivatives, reduced starch, and mixtures and/or combinations thereof. The prebiotic can be administered in a single daily dose or multiple daily doses. The inner core of the solid dosage forms can comprise from about 100 mg to about 100 g, alternatively from about 500 mg to about 50 g, and alternatively from about 1 g to about 40 g of prebiotic, per solid dosage form.

The solid dosage forms can comprise additional ingredients which can be selected from, but are not limited to: polyphenols, non-limiting examples of which can include tea extract, rosemary extract, rosemarinic acid, coffee extract, caffeine, caffeic acid, turmeric extract, blueberry extract, grape extract, grape seed extract, soy extract and combinations thereof; amino-acids; fatty acids; carotenoids; anti-oxidants; and combinations thereof. The additional ingredients may be administered in a single daily dose or multiple daily doses.

The solid dosage forms can also comprise an excipient as would be understood by those of skill in the art with respect to production of various types of dosage units. In one example, the inner core comprises the excipient. Non-limiting examples of excipients include microcrystalline cellulose, dicalcium phosphate, stearic acid, magnesium stearate, corn starch, lactose, sodium crosscarmellose, sodium starch glycolate, polyvinylpyrollidone, gelatin, and combinations thereof. The inner core of the solid dosage forms can comprise from about 1% to about 99%, alternatively from about 2% to about 70%, alternatively from about 3% to about 50%, alternatively from about 5% to about 30%, and alternatively from about 6% to about 25%, of the excipient, by weight of the inner core of the solid dosage form. In another example the solid dosage form comprises from about 15% to about 55% excipient, in another example from about 20% to about 45%, in another example from about 25% to about 40%, and in another example from about 30% to about 38%, by weight of the solid dosage form.

The inner core of the solid dosage forms can also comprise one or more of a wide range of optional ingredients and process aids as would be understood by those of skill in the art with respect to production of various dosage forms. Non-limiting examples of optional ingredients include plasticizers, colorants, flavorants, sweeteners, buffering agents, slip aids, carriers, pH adjusting agents, natural ingredients, stabilizers, biological additives such as enzymes (including proteases and lipases), chemical additives, coolants, chelants, denaturants, drug astringents, emulsifiers, external analgesics, fragrance compounds, humectants, opacifying agents (such as zinc oxide and titanium dioxide), antifoaming agents (such as silicone), preservatives (such as butylated hydroxytoluene (BHT) and butylated hydroxyanisole (BHA), propyl gallate, benzalkonium chloride, EDTA, benzyl alcohol, potassium sorbate, parabens and mixtures thereof), reducing agents, solvents, hydrotropes, solublizing agents, suspending agents (non-surfactant), solvents, viscosity increasing agents (aqueous and non-aqueous), sequestrants, keratolytics, and the like, and mixtures and/or combinations thereof. Generally, unless otherwise specified herein, the inner core of the solid dosage forms can comprise from about 0.001% to about 99%, alternatively from about 0.01% to about 80%, alternatively from about 0.01% to about 50%, and alternatively from about 0.01% to about 10%, of optional ingredient(s) by weight of the composition of the inner core of the solid dosage form.

Sweeteners and flavors may optionally be added to the inner core of the solid dosage compositions and/or the film coating honey compositions of the present invention. Suitable flavors for use herein include aspartame, saccharin and its salts, Sucralose™ (sold by the McNeil Specialty Products Co., New Brunswick, N.J.); Prosweet™ (sold by the Virginia Dare Extract Co., New York, N.Y.); Magnasweet™ (sold by MAFCO Worldwide Corp., Licorice Division, Camden, N.J.); ammonium glycyrrhizinate and its salts, Talin™ (thaumatin) and its diluted products, such as Talin GA90, (sold by the Talin Food Company, Birkenhead, England); and Acesulfame K, or mixtures thereof.

The inner core and the film coating of the present invention may further comprise sensory agents. Suitable non-limiting examples of sensory agents can include sensory agents selected from the group consisting of coolants, salivating agents, warming agents or mixtures thereof. When present, these agents are preferably present in the compositions at a level of from about 0.001% to about 10%, preferably from about 0.1% to about 1%, by weight of the composition.

Non-limiting examples of suitable cooling agents include but are not limited to, carboxamides, menthols, thymol, camphor, phenol, eucalyptus oil, benzyl alcohol, salicyl alcohol, ethanol, clove bud oil, and hexylresorcinol, ketals, diols, and mixtures thereof. Preferred warming agents include thymol, camphor, capsicum, phenol, benzyl alcohol, salicyl alcohol, ethanol, clove bud oil, and hexylresorcinol, nicotinate esters such as benzyl nicotinate, ketals, diols, capsicum, and mixtures thereof.

Coolants can include the paramenthan carboxyamide agents such as N-ethyl-p-menthan-3-carboxamide (known as "WS-3" supplied by Sterling Organics), taught by U.S. Pat. No. 4,136,163, issued Jan. 23, 1979, to Watson et al. and carboxyamide agent is N,2,3-trimethyl-2-isopropylbutanamide, known as "WS-23", or mixtures of WS-3 and WS-23. In one example, the solid dosage form comprises WS-3.

Additional coolants can be selected from the group consisting of menthol, 3-1-menthoxypropane-1,2-diol, known as TK-10 or Cool Agent 10, supplied by Takasago Perfumery Co., Ltd., Tokyo, Japan, menthone glycerol acetal known as MGA, manufactured by Haarmann and Reimer, menthyl lactate known as Frescolat® manufactured by Haarmann and Reimer, or mixtures thereof. Additional non-limiting examples of coolants include N-(4-cyanomethylphenyl)-p-menthanecarboxamide or N-(4-cyanomethylphenyl)-5-methyl-2-(1-methylethyl)cyclohexanecarboxamide (for example, commercially available from Givaudan), N-(2-(pyridin-2-yeethyl-3-p-menthanecarboxamide (for example, commercially available from Givaudan), N-(4-sulfamoylphenyl)-p-menthanecarboxamide, N-(4-cyanophenyl)-p-menthanecarboxamide, N-(4-acetylphenyl)-p-menthanecarboxamide, N-(4-hydroxymethylphenyl)-p-menthanecarboxamide, N-(3-hydroxy-4-methoxyphenyl)-p-menthanecarboxamide, Ethyl 3-(p-menthane-3-carboxamido)acetate (for example, known as WS-5), p-Menthane-3,8-diol (for example, commercially available as PMD38 from Takasago International), Isopulegol (for example, commercially available under the name "Coolact P®" from Takasago International), (1R,2S,5R)-2-isopropyl-5-methyl-N-(2-(pyridyn-2-yl)ethylcyclohexane carboxamide, (1-glyceryl-p-mentane-3-carboxylate), (ethyleneglycol-p-methane-3-carboxylate), (N-t-butyl-p-menthane-3-carboxamide), (N-(4-,ethoxyphenyl)-p-menthane-3-carboxamide), 3-(1-menthoxy)propane-1,2-diol, 3-(1-Menthoxy)-2-methylpropane-1,2-diol, menthyl pyrrolidone carboxylate) (for example, commercially available as Questice®), (1R,3R,4S)-3-menthyl-3,6-dioxaheptanoate (for example, commercially available from Firmenich), (1R, 2S,5R)-3-menthyl methoxyacetate (for example, commercially available from Firmenich), (1R,2S,5R)-3-menthyl 3,6,9-trioxadecanoate (for example, commercially available from Firmenich), (1R,2S,5R)-menthyl 11-hydroxy-3,6,9-trioxaundecanoate (for example, commercially available from Firmenich), (1R,2S,5R)-3-menthyl (2-hydroxyethoxy)acetate (for example, commercially available from Firmenich), Cubebol (for example, commercially available from Firmenich), 1-[2-hydroxyphenyl]-4-[2-nitrophenyl-]-1,2,3,6-tetrahydropyrimidine-2-one), 4-methyl-3-(1-pyrrolidinyl)-2 [5H]-furanone (for example, known as Icilin or AG-3-5), menthyl lactate, menthone glycerin acetal, L-Monomenthyl succinate, L-monomenthyl glutarate, 3-1-menthoxypropane-1,2-diol (for example, known as Coolact 10), 2-1-menthoxyethanol (for example, known as Cooltact 5), and mixtures thereof. Additional coolants are described in U.S. Pat. No. 7,414,152, US20100086498 A1 and WO2010/128026 A2. In one embodiment, the coolant is N-(4-cyanomethylphenyl)-p-menthanecarboxamide including all 8 stereoisomers arising from the 3 chiral centers. In particular, the [1R, 2S, 5R]-N-(4-cyanomethylphenyl)-p-menthanecarboxamide can be readily synthesized from natural 1-menthol.

The film coated tablets described herein can be made by any suitable tableting and coating process. Examples 1-4, described hereafter, describe a pan coating process. The film coating can be applied as a liquid film coating. In one example the liquid film coating comprises from about 8% to about 25% solids, in another example from about 12% to about 24% solids, in another example from about 13% to about 21% solids, and in another example from about 14% to about 19% solids, by weight of the liquid film coating. In one example, when the pan coating process is complete, the tablet cores have a total weight gain of about 0.5% to about 10%, in another example from about 1% to about 8%, in another example from about 2% to about 6%, and in another example from about 2.5% to about 5%. In one example, the tablet cores have a total weight gain of about 3%.

EXAMPLES

Example 1

Tablet cores are prepared by normal tableting practices on a high speed tablet press at medium compression pressure.

| Core Ingredients | % | Dose per tablet (mg) |
|---|---|---|
| Compap L APAP USP 90% USP | 53.4979 | 361.10 |
| Phenylephrine HCl USP | 0.74080 | 5.00 |
| Dextromethorphan HBr USP | 1.48150 | 10.00 |
| Microcrystalline Cellulose NF | 33.7798 | 228.00 |
| Partially Pregelatinized Starch 1500 NF | 10.0000 | 67.50 |
| Magnesium Stearate NF | 0.50000 | 3.38 |
| | 100.00 | 675.00 |

| Coating Ingredients | % |
|---|---|
| Purified Water | 85.71 |
| Opadry II Yellow 57U120009 [1] | 9.52 |
| Natural Honey Flavor 229946 [2] | 4.23 |
| Sucralose NF [3] | 0.53 |

[1] Available from Colorcon Inc.
[2] Available as a liquid from Symrise Inc.
[3] Available as a powder from Tate and Lyle Inc. Singapore PTE LTD.

The tablets are then coated in a Vector Tablet Coater LCD 5 with a 1.3 L spray pan. Prepare coating solution by weighing out the water and with mixing using for example a four blade propeller, slowly add colorant with an agitation speed of 200-700 rpm for 45 minutes or until completely dispersed. Slowly add flavor and sweetener with mixing for about 15 minutes until homogeneous. At this point the 14.3% solids coating solution is ready for use for coating tablet cores.

Weigh out about 1 kg of tablets and place in the tablet coater. Set bed temperature to 45° C. and inlet temperature to 75° C. Allow the tablets to come to a bed temperature of 40-50° C. at a pan speed of 12 rpm and equilibrate for 15 minutes. The spray nozzle is centered in the pan with a working distance of 7.5 cm from the tablet bed at a 45 degree angle or at just the peak of the tablet fall in the coater. At the start spray about 3 grams per minute until the coating is evenly found on the tablet cores and then increase the level of coating solids sprayed to between 7 and 8 grams per minute. The total spraying time of the coating is typically less than about 30 minutes to achieve the final tablets weight gain of 3%. Time and volume of film coat applied varies depending on what is the desired weight gain.

Example 2

Tablet cores are prepared by normal tableting practices on a high speed tablet press at medium compression pressure. These tablets are then coated in a Vector Tablet Coater LCD 5 with a 1.3 L spray pan.

Prepare coating solution by weighing out the water and with mixing using for example a four blade propeller, slowly add colorant with an agitation speed of 200-700 rpm for 45 minutes or until completely dispersed. Slowly add flavor and sweetener with mixing for about 15 minutes until homogeneous. At this point the coating is ready for use for coating tablet cores.

Weigh out about 1 kg of tablets and place in the tablet coater. Set bed temperature to 45° C. and inlet temperature to 75° C. Allow the tablets to come to a bed temperature of 40-50° C. at a pan speed of 12 rpm and equilibrate for 15 minutes. The spray nozzle is centered in the pan with a working distance of 7.5 cm from the tablet bed at a 45 degree angle or at just the peak of the tablet fall in the coater. At the start spray about 3 grams per minute until the coating is evenly found on the tablet cores and then increase the level of coating solids sprayed to between 7 and 8 grams per minute. The total spraying time of the coating is less than 30 minutes wherein the final weight gain of the tablet by coating is 3.0%.

| Coating Ingredients | % |
|---|---|
| Purified Water | 83.6 |
| Opadry II Yellow 57U120009 [1] | 9.53 |
| Natural Honey Flavor 229946 [2] | 6.35 |
| Sucralose NF [3] | 0.53 |

[1] Available from Colorcon Inc.
[2] Available as a liquid from Symrise Inc.
[3] Available as a powder from Tate and Lyle Inc. Singapore PTE LTD.

The coating solution is prepared by weighing out the water and mixed with a four blade propeller the colorant is added slowly with agitation speed of 200-700 rpm for 45 minutes to disperse. Then the flavor and sweetener are added slowly and mixed for another 15 minutes. The 16.4% solids dispersion is then ready to be sprayed on the tablet cores.

Weigh out about 1 kg of tablets and place in the tablet coater. Set bed temperature to 45° C. and inlet temperature to 75° C. Allow the tablets to come to a bed temperature of 40-50° C. at a pan speed of 12 rpm and equilibrate for 15 minutes. The spray nozzle is centered in the pan with a working distance of 7.5 cm from the tablet bed at a 45 degree angle or at just the peak of the tablet fall in the coater. At the start the amount of coating solids sprayed per minute is about 3 grams and is increased to between 7 and 8 grams per minute after a base coat is applies to the tablets. The total spraying time of the coating is typically less than about 30 minutes to achieve the final tablets weight gain of 3%. Time and volume of film coat applied varies depending on what is the desired weight gain.

Example 3

Tablet are prepared by normal tableting practices on a high speed tablet press at medium compression pressure. These tablets are then coated in a Vector Tablet Coater LCD 5 with a 1.3 L spray pan.

Prepare coating solution by weighing out the water and with mixing using for example a four blade propeller, slowly add colorant with an agitation speed of 200-700 rpm for 45 minutes or until completely dispersed. Slowly add flavor and sweetener with mixing for about 15 minutes until homogeneous. At this point the 18.5% solids coating solution is ready for use for coating tablet cores.

Weigh out about 1 kg of tablets and place in the tablet coater. Set bed temperature to 45° C. and inlet temperature to 75° C. Allow the tablets to come to a bed temperature of 40-50° C. at a pan speed of 12 rpm and equilibrate for 15 minutes. The spray nozzle is centered in the pan with a working distance of 7.5 cm from the tablet bed at a 45 degree angle or at just the peak of the tablet fall in the coater. At the start spray about 3 grams per minute until the coating is evenly found on the tablet cores and then increase the level of coating solids sprayed to between 7 and 8 grams per minute. The total spraying time of the coating is typically less than about 30 minutes to achieve the final tablets weight gain of 3%. Time and volume of film coat applied varies depending on what is the desired weight gain.

| Coating Ingredients | % |
|---|---|
| Purified Water | 81.48 |
| Opadry II Yellow 57U120009 [1] | 9.53 |
| Nat. Honey Flavor 229946 [2] | 8.46 |
| Sucralose NF [3] | 0.53 |

[1] Available from Colorcon Inc.
[2] Available as a liquid from Symrise Inc.
[3] Available as a powder from Tate and Lyle Inc. Singapore PTE LTD.

The coating solution is prepared by weighing out the water and mixed with a four blade propeller the colorant is added slowly with agitation speed of 200-700 rpm for 45 minutes to disperse. Then the flavor and sweetener are added slowly and mixed for another 15 minutes. The dispersion is then ready to be sprayed on the tablet cores.

Weigh out about 1 kg of tablets and place in the tablet coater. Set bed temperature to 45° C. and inlet temperature to 75° C. Allow the tablets to come to a bed temperature of 40-50° C. at a pan speed of 12 rpm and equilibrate for 15 minutes. The spray nozzle is centered in the pan with a working distance of 7.5 cm from the tablet bed at a 45 degree angle or at just the peak of the tablet fall in the coater. At the start the amount of coating solids sprayed per minute is about 3 grams and is increased to between 7 and 8 grams per minute after a base coat is applies to the tablets. The total spraying time of the coating is less than 30 minutes. The total spraying time of the coating is typically less than about 30 minutes to achieve the final tablets weight gain of 3%. Time and volume of film coat applied varies depending on what is the desired weight gain.

Example 4

Tablet cores are prepared by normal tableting practices on a high speed tablet press at medium compression pressure. These tablets are the coated in a Vector Tablet Coater LCD 5 with a 1.3 L spray pan.

Prepare coating solution by weighing out the water and with mixing using for example a four blade propeller, slowly add colorant with an agitation speed of 200-700 rpm for 45 minutes or until completely dispersed. Slowly add flavor and sweetener with mixing for about 15 minutes until homogeneous. At this point the coating solution containing 20.6% solids is ready for use for coating tablet cores.

Weigh out about 1 kg of tablets and place in the tablet coater. Set bed temperature to 45° C. and inlet temperature to 75° C. Allow the tablets to come to a bed temperature of 40-50° C. at a pan speed of 12 rpm and equilibrate for 15 minutes. The spray nozzle is centered in the pan with a working distance of 7.5 cm from the tablet bed at a 45 degree angle or at just the peak of the tablet fall in the coater. At the start spray about 3 grams per minute until the coating is evenly found on the tablet cores and then increase the level of coating solids sprayed to between 7 and 8 grams per minute. The total spraying time of the coating is typically less than about 30 minutes to achieve the final tablets weight gain of 3%. Time and volume of film coat applied is varies depending on what is the desired weight gain.

| Coating Ingredients | % |
|---|---|
| Purified Water | 79.37 |
| Opadry II Yellow 57U120009 [1] | 9.53 |
| Natural Honey Flavor 229946 [2] | 10.57 |
| Sucralose NF [3] | 0.53 |

[1] Available from Colorcon Inc.
[2] Available as a liquid from Symrise Inc.
[3] Available as a powder from Tate and Lyle Inc. Singapore PTE LTD.

The coating solution is prepared by weighing out the water and mixed with a four blade propeller the colorant is added slowly with agitation speed of 200-700 rpm for 45 minutes to disperse. Then the flavor and sweetener are added slowly and mixed for another 15 minutes. The dispersion is then ready to be sprayed on the tablet cores.

Weigh out about 1 kg of tablets and place in the tablet coater. Set bed temperature to 45° C. and inlet temperature to 75° C. Allow the tablets to come to a bed temperature of 40-50° C. at a pan speed of 12 rpm and equilibrate for 15 minutes. The spray nozzle is centered in the pan with a working distance of 7.5 cm from the tablet bed at a 45 degree angle or at just the peak of the tablet fall in the coater. At the start the amount of coating solids sprayed per minute is about 3 grams and is increased to between 7 and 8 grams per minute after a base coat is applies to the tablets. The total spraying time of the coating is typically less than about 30 minutes to achieve the final tablets weight gain of 3%. Time and volume of film coat applied varies depending on what is the desired weight gain.

Example 5

Tablet cores are prepared by normal tableting practices on a high speed tablet press at medium compression pressure. These tablets are then coated in a Vector Tablet Coater LCD 5 with a 1.3 L spray pan.

Prepare coating solution by weighing out the water and with mixing using for example a four blade propeller, slowly add colorant with an agitation speed of 200-700 rpm for 45 minutes or until completely dispersed. At this point the coating is ready for use for coating tablet cores.

Weigh out tablets 1 kg of tablets and place in the tablet coater. Set bed temperature to 45° C. and inlet temperature to 75° C. Allow the tablets to come to a bed temperature of 40-50° C. at a pan speed of 12 rpm and equilibrate for 15 minutes. The spray nozzle is centered in the pan with a working distance of 7.5 cm from the tablet bed at a 45 degree angle or at just the peak of the tablet fall in the coater. At the start spray about 3 grams per minute until the coating is evenly found on the tablet cores and then increase the level of coating solids sprayed to between 7 and 8 grams per minute. The spraying takes place to a final weight gain on the tablet of about 3%.

| Coating Ingredients | % |
|---|---|
| Purified Water | 90 |
| Opadry II Yellow 57U120009 [1] | 10 |

[1] Available from Colorcon Inc.

Example 6

| Ingredient | % w/w |
| --- | --- |
| Water, purified | 47.278 |
| High Fructose Corn Syrup | 29.860 |
| Polyethylene glycol 400 | 8.531 |
| Propylene glycol | 6.399 |
| Xanthan gum [1] | 0.256 |
| Pectin | 0.064 |
| Acetaminophen | 1.173 |
| Dextromethorphan hydrobromide | 0.059 |
| Doxylamine succinate | 0.022 |
| Sodium citrate dihydrate | 0.188 |
| Citric acid anhydrous | 0.229 |
| Sodium benzoate | 0.085 |
| Potassium sorbate | 0.256 |
| Natural Honey Flavor 229946 [2] | 5.000 |
| Flavors/sensates | 0.600 |

[1] Available from ProTec Ingredia Ltd, UK as Xanthan gum NovaXan 80T [1]
[2] Available as a liquid from Symrise Inc.

The liquid composition of Example 6 can be made by first mixing the water and high fructose corn syrup to make the water phase. Separately, propylene glycol, polyethylene glycol, flavors/sensates, natural honey flavor, acetaminophen, dextromethorphan hydrobromide and doxylamine succinate are combined and mixed to form a glycol premix. Xanthan gum and pectin are added to the glycol pre-mix and mixed until dispersed. The glycol premix is added to the water phase and mixed to combine. The sodium citrate dihydrate, citric acid anhydrous, sodium benzoate and potassium sorbate are added to the batch and mixed until dissolved.

Honey Flavor Consumer Study

The solid dose honey coated tablet of Example 1 is compared to a liquid composition containing 2.5% w/w liquid honey of Example 6.

Participants suffering from cold-related symptoms within the last 36 hours, with at least 2 symptoms selected from body aches, chest congestion, cough, fatigue, fever, headache, post nasal drip, runny nose, sneezing, sinus congestion/nasal congestion/stuffy nose, sinus pressure, sinus pain, or sore throat, and intend to treat their symptoms with an over-the-counter cough cold product are recruited. Participants include both males and females, over the age of 18. Participants are divided into two groups. The first group of participants (n=77) are directed to ingest 2 Solid Dose caplets per dose, with water as they would normally treat their cold/flu symptoms, over 3 days. Alternatively, the second group of participants (n=200) are directed to ingest 30 ml of the Liquid Composition per dose, as they would normally treat their cold/flu symptoms, over 3 days.

Following completion of the study, participants are asked to rate the honey flavor of the Example 1, the solid dose tablet, or Example 6, the liquid composition, using a scale of Excellent (=100), Very Good (=75), Good (=50), Fair (=25) or Poor (=0).

Then the scores, are averaged to determine the final score for each example. The liquid composition of Example 6 had a score of 66 and the Solid Dose of Example 1 had a score of 82 the difference is statistically significant ($p<0.05$).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

It is noted that terms like "preferably," "generally," "commonly," "typically" and "alternatively" are not utilized herein to limit the scope of the claimed embodiments or to imply that certain features are critical, essential, or even important to the structures or functions. Rather, these terms are merely intended to highlight alternative or additional features that may or may not be utilized in a particular embodiment. For the purposes of describing and defining the various embodiments it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

What is claimed is:

1. A tablet comprising:
   a film coating wherein the film coating comprises from about 10% to about 25% sticky natural honey; and
   an inner core comprising an active selected from the group consisting of decongestants, pain relievers, antitussives, antihistamines, anesthetics, expectorants and combinations thereof;
   wherein the tablet has a static coefficient of friction value from about 0.15 to about 0.40.

2. The tablet of claim 1 wherein the film coating comprises from about 13% to about 18% sticky natural honey.

3. The tablet of claim 1 wherein the film coating further comprises from about 0.05% to about 5% sweetener, by weight of the film coating.

4. The tablet of claim 1 wherein the anesthetic is selected from the group consisting of phenol, menthol, dyclonine HCl, benzocaine, lidocaine, hexylresorcinol, and combinations thereof.

5. The tablet of claim 1 wherein the active comprises a decongestant, a pain reliever, and an antitussive.

6. The tablet of claim 5 wherein the decongestant is phenylephrine HCl, the pain reliever is acetaminophen, and the antitussive is dextromethorphan HBr.

7. The tablet of claim 1 wherein the inner core further comprises a vitamin.

8. The tablet of claim 1 further comprising a mineral, metal, or element selected from the group consisting of zinc, iron, calcium, iodine, copper, selenium and combinations thereof.

9. The tablet of claim 1 further comprising a sensory agent selected from the group consisting of coolants, salivating agents, warming agents and combinations thereof.

10. The tablet of claim 1 wherein the inner core further comprises an excipient selected from the group consisting of microcrystalline cellulose, dicalcium phosphate, stearic acid, magnesium stearate, corn starch, lactose, sodium crosscarmellose, sodium starch glycolate, polyvinylpyrollidone, gelatin, and combinations thereof.

11. A tablet comprising:
 a film coating wherein the film coating comprises from about 10% to about 25% sticky natural honey; and
 an inner core comprising dextromethorphan HBr;
 wherein the tablet has a static coefficient of friction value from about 0.15 to about 0.40.

12. The tablet of claim 11 wherein the inner core further comprises guaifenesin.

13. The tablet of claim 11 wherein the film coating further comprises from about 0.5% to about 3.0% of a colorant, by weight of the film coating.

14. The solid dosage form of claim 11 wherein the film coating further comprises propylene glycol.

15. A tablet comprising:
 a film coating wherein the film coating comprises from about 10% to about 25% sticky natural honey; and
 an inner core comprising diphenhydramine; wherein the tablet has a static coefficient of friction value from about 0.15 to about 0.40.

16. The tablet of claim 15 wherein the inner core further comprises 5 mg phenylephrine HCl.

17. The tablet of claim 15 wherein the inner core further comprises from about 200 mg to about 350 mg acetaminophen.

18. The tablet of claim 15 wherein the film coating further comprises from about 0.05% to about 5% sweetener, by weight of the film coating.

19. The tablet of claim 15 wherein the inner core further comprises an excipient selected from the group consisting of microcrystalline cellulose, dicalcium phosphate, stearic acid, magnesium stearate, corn starch, lactose, sodium crosscarmellose, sodium starch glycolate, polyvinylpyrollidone, gelatin, and combinations thereof.

* * * * *